(12) United States Patent
Chen et al.

(10) Patent No.: US 6,602,522 B1
(45) Date of Patent: *Aug. 5, 2003

(54) PHARMACEUTICAL FORMULATION FOR ACID-LABILE COMPOUNDS

(75) Inventors: Chih-Ming Chen, Davie, FL (US); Joseph Chou, Coral Springs, FL (US); Unchalee Kositprapa, Fort Lauderdale, FL (US)

(73) Assignee: Andrx Pharmaceuticals L.L.C., Davie, FL (US)

( * ) Notice: Subject to any disclaimer, the term of this patent is extended or adjusted under 35 U.S.C. 154(b) by 33 days.

This patent is subject to a terminal disclaimer.

(21) Appl. No.: 09/597,206

(22) Filed: Jun. 20, 2000

Related U.S. Application Data

(63) Continuation-in-part of application No. 09/335,575, filed on Jun. 18, 1999, now Pat. No. 6,077,541, which is a division of application No. 08/970,489, filed on Nov. 14, 1997, now Pat. No. 6,096,340, and a continuation-in-part of application No. 09/143,167, filed on Aug. 28, 1998, now Pat. No. 6,174,548.

(51) Int. Cl.$^7$ .............................. A61K 9/36; A61K 9/14; A61K 9/24; A61K 9/28; A61K 9/30
(52) U.S. Cl. ...................... 424/480; 424/474; 424/475; 424/476; 424/479
(58) Field of Search ................................. 424/480, 479, 424/475, 474, 476

(56) References Cited

U.S. PATENT DOCUMENTS

| | | | | |
|---|---|---|---|---|
| 5,219,870 A | * | 6/1993 | Kim ........................... | 514/338 |
| 5,753,265 A | * | 5/1998 | Bergstrand et al. ......... | 424/474 |
| 5,846,562 A | * | 12/1998 | Yanai et al. ................. | 424/451 |
| 6,077,541 A | * | 6/2000 | Chen et al. .................. | 424/480 |
| 6,096,340 A | * | 8/2000 | Chen et al. .................. | 424/480 |
| 6,174,548 B1 | * | 1/2001 | Chen et al. .................. | 424/474 |

* cited by examiner

*Primary Examiner*—Shelley A. Dodson
(74) *Attorney, Agent, or Firm*—Ted W. Whitlock; David W. Barman

(57) ABSTRACT

A pharmaceutical composition of omeprazole for oral administration is described which includes:

(a) a tabletted core component containing a therapeutically effective amount of a acid-labile compound, e.g., substituted benzamidazole such as omeprazole, an optional surface active agent, a filler, a pharmaceutically acceptable alkaline agent, and a binder; and (b) a single layer of coating on said core which comprises a layer of an enteric coating agent.

24 Claims, No Drawings

PHARMACEUTICAL FORMULATION FOR ACID-LABILE COMPOUNDS

CROSS-REFERENCE TO RELATED APPLICATION

This is a continuation-in-part of U.S. patent application Ser. No. 09/335,575, filed Jun. 18, 1999, now U.S. Pat. No. 6,077,541 which is a divisional of U.S. patent application Ser. No. 08/970,489, filed Nov. 14, 1997, now U.S. Pat. No. 6,096,340 and is a continuation-in part of U.S. patent application Ser. No. 09/143,167, filed Aug. 28, 1998, now U.S. Pat. No. 6,174,548.

BACKGROUND OF THE INVENTION

The present invention relates to a stable tablet formulation of a pharmaceutical compound or composition, and particularly relates to a stable formulation for an acid-labile compound, e.g., a substituted benzamidazole, such as the proton pump inhibitor, omeprazole.

It is well known that certain therapeutic compounds are sensitive to acidic conditions and can degrade after contact with an acid. For example, the well-known compound, omeprazole, degrades and will not function in its intended manner when it contacts the acidic conditions of the stomach. Historically, alkaline materials were added to a core of omeprazole to buffer or neutralize the environment, i.e., the acidic conditions of the stomach, to which the compound was exposed during use. Enteric coatings were later applied over the omeprazole core to prevent the acidic pH conditions of the stomach from contacting the omeprazole. Providing an enteric coating over the omeprazole core can be satisfactory if the product is administered within a short time after its manufacture. However, if the product is stored under ambient conditions, the acidic residue of the enteric coating can degrade the omeprazole active ingredient before it is administered to a patient.

To solve this problem, certain formulations in the prior art have used a separate layer of a coating agent to coat a pellet core comprising omeprazole and an alkaline material. These coated pellets are thereafter further coated with an additional layer of enteric coating. This technique of providing a separate or second additional coating, i.e., a dual layer, as described in U.S. Pat. No. 4,786,505, can be disadvantageous in that it requires two separate coating steps in its manufacture. Thus, the length of the manufacturing process for the product and the resulting costs are increased.

The applicants have surprisingly discovered a novel formulation which (1) avoids the need to use a separate or dual coating layer to physically isolate an acid-labile active ingredient, for example, substituted benzamidazole such as omeprazole, from the enteric coating layer; and (2) provides a means for manipulating or controlling bioavailability of the active ingredient by providing cohesiveness of the powdered ingredients upon tablet disintegration.

In addition, the subject formulation can advantageously provide a tablet dosage form which is bioequivalent to a capsule dosage form of the same or substantially similar strength. The tablet dosage form can further be advantageous in that the manufacturing process can require fewer steps, e.g., eliminate the need for pellet formation and/or coating of those pellets, and there is no need for the additional expense of providing capsule shells.

SUMMARY OF THE INVENTION

The present invention concerns a novel dosage form or formulation for an acid-labile compound, e.g., a substituted benzamidazole such as omeprazole. The subject invention involves the use of an enteric coating agent applied to a core of an active ingredient, such as omeprazole, and a particular binder as a suspension in a suitable solvent. The subject invention further concerns a formulation which employs a unique combination of water-soluble and water insoluble binder which can lend certain advantages to the pharmacokinetics of the active ingredient.

In a preferred embodiment, the subject formulation comprises:

(a) a compressed tablet core made from a granulation comprising
  (i) a therapeutically effective amount of an active ingredient, e.g., an acid-labile compound such as a substituted benzamidazole,
  (ii) an optional surface active agent,
  (iii) a filler,
  (iv) a pharmaceutically acceptable alkaline agent, and
  (v) a binder; and (b) a single layer of coating on said core, the coating comprising an enteric coating agent.

Accordingly, it is an object of this invention to provide a pharmaceutical dosage formulation of an acid-labile compound, e.g., a substituted benzamidazole such as omeprazole, which is stable upon prolonged storage, is stable when administered to a patient, and is capable of providing the desired therapeutic effect.

It is also an object of this invention to provide a tablet dosage form of an acid-labile compound, e.g., a substituted benzamidazole such as omeprazole, which is bioequivalent to beaded capsule dosage forms which have an additional intermediate layer of an inert coating material.

It is a further object of this invention to provide a pharmaceutical dosage form of an acid-labile compound, e.g., a substituted benzamidazole such as omeprazole, which is bioequivalent to dosage forms comprising a multiparticulate drug delivery system.

Yet another object of this invention is to provide a stable dosage form of an acid-labile compound, e.g., omeprazole, which may be produced without the need for an intermediate coating layer that separates the tablet core from the enteric coating layer.

These and other objects of the invention will become apparent from a review of the appended specification.

DETAILED DESCRIPTION OF THE INVENTION

The formulation of the subject invention is preferably based on a compressed tablet core formed from a granulation which comprises an acid-labile compound as an active ingredient, e.g., a substituted benzamidazole such as omeprazole, an optional surface-active agent, a filler, an alkaline material, and a binder.

The granulation core can comprise from about 5 to about 70 wt % and, preferably, can comprise about 10 to about 30 wt % of active ingredient. The formulation is advantageously adapted for use with an acid-labile active ingredient, and is preferably used with a substituted benzamidazole. Substituted benzamidazole are commonly known in the art and include, but are not limited to, proton pump inhibitors, e.g., omeprazole, lansoprazole, pantoprazole, perprazole, and the like, as well as pharmaceutically acceptable salts, isomers, or derivatives thereof.

The surface-active agent can be any pharmaceutically acceptable, non-toxic surfactant, e.g., polysorbate 80 (Tween 80), or the like. The surface-active agent may be present at a level of up to about 5 wt % and, preferably, from about 0.20 to about 2.0 wt %, based on the total weight of the granulation.

The alkaline material can be sodium, potassium, calcium, magnesium or aluminum salts of phosphoric acid, carbonic acid, or citric acid, or can be aluminum/magnesium compounds such as $Al_2O_3 \cdot 6MgO \cdot CO_2 \cdot 12H_2O$, $(Mg_6Al_2(OH)_{16}CO_3 \cdot 4H_2O)$, or $MgO \cdot Al_2O_3 \cdot 2SiO_2 \cdot nH_2O$ where n is a whole integer of 2 or more. Alternatively, the alkaline material can be lysine or arginine, or can be an antacid such as aluminum hydroxide, calcium hydroxide, magnesium hydroxide, or magnesium oxide. The alkaline agent is preferably provided at about 10 to about 80 wt % based on the total weight of the granulation, and would be understood by those of ordinary skill in the art to depend on the relative strength of the alkaline material. For example, arginine is typically utilized in the formulation from about 10 to about 60 wt %, and is preferably formulated at about 30 to about 55 wt %.

The binder can be any pharmaceutically acceptable, nontoxic binder such as a water-soluble polymer, e.g., polyvinyl alcohol, polyvinylpyrrolidone, methylcellulose, hydroxypropyl cellulose, hydroxymethyl cellulose, or a water-insoluble polymer, e.g., a polymethacrylic acid copolymer such as Eudragit NE30D. Eudragit NE30D is commercially available as a 30% aqueous dispersion. Preferably, the subject formulation comprises the unique combination of both a water-soluble and water-insoluble binder. The binder, whether as a water-soluble, water-insoluble, or as a combination, is preferably provided up to about 10 wt % in an aqueous medium such as water, or as an aqueous dispersion. More preferably, the binder is provided from about 0.25 to 7.5 wt % based on the total weight of the granulation.

A filler can also be used as a granulation substrate. As well understood in the art, sugars such as lactose, dextrose, sucrose, maltose, or microcrystalline cellulose or the like can be used as fillers in the granulation composition. The filler preferably can be provided from about 20 to 50 wt %, and more preferably about 25 to 40 wt % based on the total weight of the granulation.

A tablet disintegrant, e.g., cornstarch, potato starch, croscarmelose sodium, Crospovidone, or sodium starch glycolate, can also be included in the subject formulation in an effective amount. An effective amount of tablet disintegrant can be provided at about 1 to about 15 wt %, preferably from about 3 to about 8 wt %, based on the total weight of the granulation.

The enteric coating agent can be any pharmaceutically acceptable material which resists acid up to a pH of about 5.0 or higher. Preferably, the enteric coating ingredient is selected from cellulose acetate phthalate, hydroxypropylmethyl cellulose phthalate, polyvinyl acetate phthalate, carboxymethylethylcellulose, Eudragit NE30D, Eudragit L (polymethacrylic acid:methylmethacrylate, 1:1 ratio; MW (No. Av. 135,000—USP Type A)) or Eudragit S (polymethacrylic acid:methylmethacrylate, 1:2 ratio MW (No. Av. 135,000—USP Type B)) and, most preferably, can be a mixture thereof. For example, Eudragit L100–55 is a 100% polymer solids product while the Eudragit L30–55 product is a 30% w/w aqueous dispersion of the polymer.

The enteric coating agent can also include an inert processing aid in an amount from about 10 to about 50 wt %, and preferably from about 20 to about 40 wt %, based on the total weight of the acid resisting component and the inert processing aid. The inert processing aid can include finely divided forms of talc, silicon dioxide, magnesium stearate or the like.

Typical solvents which may be used to apply the acid resisting component-inert processing aid mixture include isopropyl alcohol, acetone, methylene chloride, the like. Generally the acid-resistant component/inert processing aid mixture will be employed from about 5 to about 20 wt % based on the total weight of the solvent and the acid-resistant component/inert processing aid.

The enteric coating can optionally comprise a plasticizer. Suitable plasticizers for use in the enteric coating include acetyl triethyl citrate, dibutyl phthalate, tributyl citrate, triethyl citrate, acetyl tributyl citrate, propylene glycol, triacetin, polyethylene glycol and diethyl phthalate. The amount of plasticizer can vary, but will typically be present in amounts up to about 40% w/w based upon the weight of acid resisting component of the coating. More preferably, the plasticizer can be provided at about 10–20% w/w based upon the weight of the acid resisting component.

The granulation is preferably formed by combining the alkaline agent, the active ingredient, e.g., omeprazole, the surface active agent, and the binder with an acceptable solvent. An acceptable solvent can be any low viscosity medium such as water, isopropyl alcohol, acetone, ethanol or the like. Use of solvents such as water usually requires, a solvent weight about three times the weight of the dry components of the coating composition.

After the granulation is formed and dried, the granulation can be tableted by standard procedures as accepted in the art. The tablets can then be directly coated with the enteric coating agent, employing standard coating procedures. A color-imparting agent may be added to the enteric coating agent mixture or a rapidly dissolving seal coat containing color may be coated over the enteric coating agent layer provided that the seal coat is compatible with and does not affect the dissolution of the enteric coating layer. The rapidly dissolving seal coat can, for example, comprise Opadry pink which comprises approximately 91 wt % hydroxypropyl methylcellulose (E-6), color, and about 9 wt % polyethylene glycol applied as a 8–15% w/w solution in purified water. In addition, the color may be provided as "Chromateric" which is available from Crompton & Knowles. This product contains water, talc, $TiO_2$, triethyl citrate, propylene glycol, synthetic red iron oxide, potassium sorbate, xanthan gum, sodium citrate, and synthetic yellow iron oxide. If desired, conventional sugar based seal coats can be used which contain FDA-certified dyes.

EXAMPLES

Example 1

A. Granulation.

A granulation comprising an acid-labile active ingredient (the "active ingredient granule") is formed in a fluid bed coater using a top spray granulation-forming suspension having micronized active ingredient, e.g., omeprazole. 5% w/w polyvinyl pyrrolidone; 2% w/w L-arginine; 0.5% w/w polysorbate 80; 0.4% w/w polymethacrylic acid copolymer, e.g., Eudragit NE30D; and purified water. The suspension is sprayed onto a mixture of microcrystalline cellulose and 92% w/w of the total amount of L-arginine. The formulation for making the granulation using omeprazole as the active ingredient has the following composition.

| | Wt. | % |
|---|---|---|
| Povidone, USP (Plasdone K30) | 97.6 g | 5.37 |
| Microcrystalline cellulose (Avicel PH101) | 465.7 g | 25.62 |
| L-arginine, USP/FCC | 731.7 g | 40.25 |
| Omeprazole, (USP, micronized)[1] | 487.8 g | 26.84 |
| Polysorbate 80 | 9.7 g | 0.53 |
| Methylmethacrylic acid (Eudragit NE30D) | 25.2 g | 1.39 |

[1]95% of the particles exhibit a particle size of less than 15 microns

B. Tableting.

The granulation is formed into tablets comprising 20 mg of active ingredient hereinafter, ("the omeprazole tablet") by standard tableting procedures. Specifically, the granules comprising omeprazole were mixed with Crospovidone and microcrystalline cellulose (Avicel PH101), then with glyceryl monostearate, in the following amounts:

| | |
|---|---|
| Omeprazole granules | 160.7 g |
| Glyceryl monostearate (EASTMAN 600P) | 13.5 g |
| Crospovidone | 79.6 g |
| Avicel PH101 | 16.2 g |

Conventional tableting procedures were performed to form the tablet as follows:

Tableting tools: 0.2812"

Target weight :124 mg/tablet

Target hardness: 7 Kp

C. Enteric coating.

An enteric coating was applied to prepare enteric coated tablets as follows: Omeprazole tablets (prepared as in Ex. 1, Sect. B., above) 105.6 g

| | |
|---|---|
| Hydroxypropyl methylcellulose phthalate 50 | 12.0 g |
| Talc | 1.2 g |
| Acetyl tributyl citrate | 1.2 g |
| Acetone | 80.0 g |
| Isopropyl alcohol | 80.0 g |

The solid coating materials were dissolved in the acetone and isopropyl alcohol and this suspension was coated onto the omeprazole tablets using a perforated pan.

Example 2

A. Granulation.

A granulation comprising an acid labile active ingredient is formed in fluid bed coater using a top spray granulation-forming suspension containing micronized active ingredient, e.g., omeprazole; 5% w/w of the total amount of L-arginine; polyvinyl pyrrolidone; sodium lauryl sulfate; a polymethacrylic acid copolymer, e.g., Eudragit NE30D; and purified water. This suspension is sprayed onto a mixture of microcrystalline cellulose, 95% w/w of the total amount of L-arginine and sodium starch glycolate. The formulation for making the granulation has the following composition:

| | Wt. | % |
|---|---|---|
| Eudragit NE30D | 33.0 g | 0.96 |
| Povidone, USP (Plasdone K30) | 98.0 g | 2.87 |
| Sodium lauryl sulfate, NF/USP | 6.0 g | 0.18 |
| Microcrystalline cellulose (Avicel PH102) | 463.0 g | 13.54 |
| L-arginine, USP/FCC | 732.0 g | 21.40 |
| Omeprazole, (USP, micronized)[1] | 488.0 g | 14.27 |
| Purified water, USP | 1600.0 g | 46.78 |

[1]95% of the particles exhibit a particle size of less than 15 microns

B. Tableting.

The granulation is formed into tablets containing 20 mg of omeprazole by first mixing the omeprazole granules with crospovidone and microcrystalline cellulose (Alvicel PH101), then with glyceryl monostearate, as follows:

| | |
|---|---|
| Omeprazole granules | 160.7 g |
| Glyceryl monostearate (EASTMAN 600P) | 13.5 g |
| Crospovidone | 79.6 g |
| Avicel PH101 | 16.2 g |

Conventional tableting procedures were carried out to obtain tablets as follows:

Tableting tools: 0.2812"

Target weight :124 mg/tablet

Target hardness: 7 Kp

C. Enteric coating.

An enteric coating was applied to prepare enteric-coated tablets as follows:

Omeprazole tablets (as prepared in Ex. 1, Sect. B., above) 124.0 g

| | |
|---|---|
| Hydroxypropyl methylcellulose phthalate 55 | 14.7 g |
| Talc | 4.2 g |
| Acetyl tributyl citrate | 2.9 g |
| Acetone | 148.0 g |
| Isopropyl alcohol | 148.0 g |

The solid coating materials were dissolved in the acetone and isopropyl alcohol and this suspension was coated onto the omeprazole tablets using a perforated pan.

D. Seal coat.

A seal coat was applied to the enteric coated tablets as follows:

| | |
|---|---|
| Enteric coated tablet | 146.0 g |
| Opadry 11 pink | 4.5 g |
| Water | 450.0 g |

The seal coat was applied onto the enteric coated omeprazole tablets using a perforated pan coater.

Example 3

A. Granulation.

A granulation comprising an acid labile active ingredient was formed in fluid bed coater using a top spray granulation-forming suspension containing micronized omeprazole; 2.0% w/w of the total amount of L-arginine; polyvinyl pyrrolidone; polysorbate 80; and a polymethyl methacrylic acid copolymer, e.g., Eudragit NE30D. The suspension is sprayed onto a mixture of microcrystalline cellulose and 95.0% w/w of the total amount of L-arginine. The formulation for making the granulation has the following composition:

|  | Wt. | % |
| --- | --- | --- |
| Povidone, USP (Plasdone K30) | 4.0 g | 4.77 |
| Polysorbate 80 (Tween 80) | 0.4 g | 0.48 |
| Eudragit NE30D | 0.4 g | 0.48 |
| L-arginine, USP/FCC | 40.0 g | 47.73 |
| Omeprazole, (USP, micronized)[2] | 20.0 g | 23.87 |
| Microcrystalline cellulose (Avicel PH102) | 19.0 g | 22.67 |

[2] 95% of the particles exhibit a particle size of less than 15 microns

B. Tableting.

The granulation is formed into tablets containing 20 mg of omeprazole by first mixing the omeprazole granules with Crospovidone XL and Avicel PH102, then with glyceryl monostearate, as follows:

| Omeprazole granules | 74.6 mg |
| --- | --- |
| Glyceryl monostearate (EASTMAN 600P) | 9.0 mg |
| Crospovidone XL | 11.8 mg |
| Microcrystalline cellulose (Avicel PH102) | 79.6 mg |

Tableting was performed using conventional tableting procedure to obtain tablets as follows:

Tableting tools: 0.3125"

Target weight : 175 mg/tab

Target hardness: 7 Kp

C. Enteric coating.

An enteric coating was applied to prepare enteric coated tablets as follows:

| Omeprazole tablets (as prepared in B., above) | 135.0 mg |
| --- | --- |
| Eudragit L30D-55 | 14.0 mg |
| Color (Chromateric ®) | 7.0 mg |

The solid coating materials were dispersed in the water and this mixture was coated onto the omeprazole tablets using a perforated pan.

Example 4

A. Granulation.

A granulation comprising an acid labile active ingredient is formed in fluid bed coater using a top spray granulation-forming suspension containing micronized active ingredient, e.g., omeprazole; 2.0% w/w of the total amount of L-arginine; polyvinyl pyrrolidone; polymethylmethacrylic acid copolymer, e.g., Eudragit NE30D; and purified water. The suspension is sprayed onto a mixture of microcrystalline cellulose and 95.0% w/w of the total amount of L-arginine. The formulation for making the granulation has the following composition, in mg/tablet:

|  | Wt. | % |
| --- | --- | --- |
| Povidone, USP (Plasdone K30) | 2.0 g | 5.42 |
| Eudragit NE30D | 0.16 g | 0.43 |
| Polysorbate 80 | 0.2 g | 0.54 |
| L-arginine, USP/FCC | 15.01 g | 40.65 |

-continued

|  | Wt. | % |
| --- | --- | --- |
| Omeprazole, (USP, micronized)[3] | 10.0 g | 27.09 |
| Microcrystalline cellulose (Avicel PH101) | 9.55 g | 25.87 |

[3] 95% of the particles exhibit a particle size of less than 15 microns

B. Tableting.

The granulation is tabletted into tablets containing 10 mg of active ingredient, e.g., omeprazole, by first mixing the omeprazole granules with sodium starch glycolatye and Avicel PH102, then with glyceryl monostearate:

| Omeprazole granules | 36.9 mg |
| --- | --- |
| Glyceryl monostearate (EASTMAN 600P) | 8.75 mg |
| Sodium starch glycolate | 10.5 mg |
| Microcrystalline cellulose (Avicel PH102) | 118.9 mg | tableting was performed by conventional procedures with the following specifications:

Tableting tools: 0.3125"

Target weight: 175 mg/tablet

Target hardness: 7 Kp

C. Enteric coating.

The tablets were coated with the same enteric coating that was applied to the tablets in Example 3, above.

Example 5

A. Granulation.

A granulation containing omeprazole is formed in fluid bed coater using a top spray granulation forming suspension containing micronized omeprazole, 2.0%w/w of the total amount of L-arginine, polyvinyl pyrrolidone, polysorbate 80, polymethacrylic acid copolymer, and purified water which is sprayed onto a mixture of microcrystalline cellulose, and 95.0%w/w of the total amount of L-arginine. The formulation for making the granulation has the following composition in mg/tablet:

|  | Wt. | % |
| --- | --- | --- |
| Povidone, USP (Plasdone K30) | 8.00 mg | 5.42 |
| Polymethacrylic a copolymer | 0.62 mg | 0.42 |
| Polysorbate 80 | 0.80 mg | 0.54 |
| L-arginine, USP/FCC | 60.0 mg | 40.65 |
| Omeprazole, (USP, micronized)[4] | 40.0 mg | 27.10 |
| Microcrystalline cellulose | 38.18 mg | 25.87 |
| Purified water, USP | n/a |  |

[4] 95% of the particles exhibit a particle size of less than 15 microns

B. Tableting.

The granulation is tabletted into tablets containing 20 mg of omeprazole by first mixing the omeprazole granules with glyceryl monostearate:

| Omeprazole granules | 147.6 mg |
| --- | --- |
| Glyceryl monostearate (EASTMAN 600P) | 7.4.1 mg |

Tableting tools: 0.2812"

Target weight : 155 mg/tab

Target hardness: 7 Kp

C. Enteric coating.

The tablets were coated with the same enteric coating that was applied to the tablets in Example 1.

Example 6

A. Granulation.

The granulation of Example 1 was prepared and tabletted into tablets containing 20.0mg of omeprazole. These tablets were coated as follows:

B. Enteric coating.

An enteric coating was applied to prepare enteric-coated tablets as follows:

| | |
|---|---|
| Omeprazole tablets (prepared above) | 124.00 mg |
| Eudragit L30D-55 | 17.00 mg |
| 1M NaOH (pH adjuster to pH 5.0) qs | na |
| Acetyl tributyl citrate | 1.70 mg |
| Talc | 3.80 mg |
| Polysorbate 80 | 1.50 mg |
| Purified water qs | na |

The coating polymer was diluted with water and the other coating materials were added. This mixture was coated onto the omeprazole tablets using a perforated pan; a seal coat was applied using the procedure of Example 2.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A stable pharmaceutical composition for an orally administered acid-labile compound used as an active ingredient, said composition comprising:

(a) a tableted core comprising an uncoated granulation of a therapeutically effective amount of the active ingredient, an optional surface active agent, a pharmaceutically acceptable alkaline agent, at least one water-soluble binder, and at least one water insoluble binder; and (b) a single layer of coating on said tableted core, said coating comprising an enteric coating agent.

2. The composition of claim 1, wherein the active ingredient is a substituted benzamidazole.

3. The composition of claim 2 wherein the substituted benzamidazole is omeprazole, lansoprazole, pantoprazole, perpazole, a pharmaceutically acceptable salt, isomer, or a derivative of said substituted benzamidazole.

4. The composition of claim 1 wherein said pharmaceutically acceptable alkaline agent is lysine, arginine, sodium, potassium, calcium, magnesium or aluminum salts of phosphoric acid, carbonic acid, or citric acid.

5. The composition of claim 1 wherein said pharmaceutically acceptable alkaline agent is aluminum hydroxide, calcium hydroxide, magnesium hydroxide, or magnesium oxide.

6. The stable pharmaceutical composition of claim 1 wherein the water insoluble binder is a polymethacrylic acid copolymer.

7. The composition of claim 1 wherein the enteric coating is cellulose acetate phthalate, hydroxypropyl methylcellulose phthalate, polyvinyl acetate phthalate, carboxymethylcellulose, or co-polymerized methacrylic acid/methacrylic acid methyl esters.

8. The composition of claim 1 wherein the enteric coating further comprises an inert processing aid.

9. The composition of claim 1 wherein the enteric coating comprises from 10 to 80 wt % by weight of the coating of an inert processing aid.

10. The composition of claim 1 wherein the surface-active agent is sodium lauryl sulfate.

11. A pharmaceutical dosage formulation which consists essentially of:

(a) a compressed tablet core comprising an acid-labile compound as an active ingredient, a binder, an alkaline agent, a filler and a surface active agent; and (b) an enteric coating agent around said core, said enteric coating comprising hydroxypropylmethyl cellulose phthalate and talc.

12. The pharmaceutical dosage formulation of claim 11 wherein the alkaline acid is a basic amino acid.

13. The pharmaceutical dosage formulation of claim 11 wherein the alkaline agent is arginine.

14. The pharmaceutical dosage formulation of claim 11, wherein the active ingredient is a substituted benzamidazole.

15. The pharmaceutical dosage formulation of claim 11 wherein the acid-labile active ingredient is a substituted benzamidizole selected from the group consisting of omeprazole, lansoprazole, pantoprazole, perpazole and a pharmaceutically acceptable base, salt, isomer, or derivative thereof.

16. The pharmaceutical dosage formulation of claim 11 wherein the binder is a combination of water-soluble and water-insoluble binders.

17. The pharmaceutical dosage formulation of claim 16, wherein the water-insoluble binder is a polymethacrylic acid copolymer.

18. A method for manipulating bioavailability of a pharmaceutical dosage formulation comprising a core having powdered components and a coating, said method comprising the step of providing at least one water-soluble binder and at least one water-insoluble binder in the core to control cohesiveness of powdered core components upon disintegration of the core.

19. The method of claim 18, wherein the water-insoluble binder is a polymethacrylic acid copolymer.

20. The method of claim 18, wherein the core comprises an acid-labile compound as an active ingredient.

21. The method of claim 20, wherein the active ingredient is a substituted benzamidazole.

22. The method of claim 20, wherein the active ingredient is omeprazole, lansoprazole, pantoprazole, perpazole or pharmaceutically acceptable base, salt, isomer, or derivatives thereof.

23. The method of claim 18, wherein the method further comprises providing a water-soluble binder in combination with the water-insoluble binder.

24. The method of claim 18, wherein the bioavailability is manipulated to delay release of the active ingredient.

* * * * *